United States Patent
Zehnacker et al.

(10) Patent No.: US 10,512,881 B2
(45) Date of Patent: *Dec. 24, 2019

(54) PROCESS FOR DEHUMIDIFYING MOIST GAS MIXTURES

(71) Applicant: Evonik Degussa GmbH, Essen (DE)

(72) Inventors: Olivier Zehnacker, Dortmund (DE);
Benjamin Willy, Düsseldorf (DE);
Xinming Wang, Kanagawa-ken (JP);
Rolf Schneider, Gründau-Rothenbergen (DE)

(73) Assignee: Evonik Degussa GmbH, Essen (DE)

( * ) Notice: Subject to any disclaimer, the term of this patent is extended or adjusted under 35 U.S.C. 154(b) by 157 days.

This patent is subject to a terminal disclaimer.

(21) Appl. No.: 15/619,577

(22) Filed: Jun. 12, 2017

(65) Prior Publication Data

US 2017/0354921 A1 Dec. 14, 2017

(30) Foreign Application Priority Data

Jun. 14, 2016 (DE) .................. 10 2016 210 484

(51) Int. Cl.
*F26B 21/06* (2006.01)
*B01D 53/26* (2006.01)
*C07D 233/56* (2006.01)
*C07F 9/09* (2006.01)
*C07F 9/11* (2006.01)
*C01D 5/00* (2006.01)

(52) U.S. Cl.
CPC .......... *B01D 53/263* (2013.01); *C07D 233/56* (2013.01); *C07F 9/091* (2013.01); *C07F 9/11* (2013.01); B01D 2252/205 (2013.01); C01D 5/00 (2013.01)

(58) Field of Classification Search
CPC .......... B01D 53/263; C07F 9/11; C07F 9/091; C07D 233/56; C01D 5/00
USPC ..................... 34/72, 76–78, 80, 82
See application file for complete search history.

(56) References Cited

U.S. PATENT DOCUMENTS

| | | | |
|---|---|---|---|
| 1,882,258 | A | 10/1932 | Randel |
| 2,516,625 | A | 7/1950 | Haury |
| 2,601,673 | A | 6/1952 | McMillan et al. |
| 2,802,344 | A | 8/1957 | Witherell |
| 3,276,217 | A | 10/1966 | Bourne et al. |
| 3,317,654 | A | 5/1967 | Yonkers |

(Continued)

FOREIGN PATENT DOCUMENTS

| | | |
|---|---|---|
| CA | 2 817 704 | 5/2012 |
| CN | 1076380 A | 9/1993 |

(Continued)

OTHER PUBLICATIONS

English language translation of the German Search Report for corresponding German application DE 10 2016 210 484.5, filed Jun. 14, 2016.

(Continued)

*Primary Examiner* — John P McCormack
(74) *Attorney, Agent, or Firm* — Law Office of: Michael A. Sanzo, LLC

(57) ABSTRACT

The invention relates to a process for dehumidifying a moist gas mixture. The invention further relates to an apparatus for dehumidifying a moist gas mixture and to the use of said apparatus in the process according to the invention.

20 Claims, 2 Drawing Sheets

(56) References Cited

U.S. PATENT DOCUMENTS

| | | |
|---|---|---|
| 3,580,759 A | 5/1971 | Albertson et al. |
| 3,609,087 A | 9/1971 | Chi et al. |
| 3,927,151 A | 12/1975 | Ishmail |
| 4,046,719 A | 9/1977 | Stanaback |
| 4,079,263 A | 3/1978 | Inoue |
| 4,094,957 A | 6/1978 | Sartori et al. |
| 4,106,904 A | 8/1978 | Oude Alink et al. |
| 4,112,051 A | 9/1978 | Sartori et al. |
| 4,152,900 A | 5/1979 | Chopra et al. |
| 4,152,901 A | 5/1979 | Munters |
| 4,201,721 A | 5/1980 | Hallgren |
| 4,217,238 A | 8/1980 | Satori et al. |
| 4,251,494 A | 2/1981 | Say |
| 4,360,363 A | 11/1982 | Ferrin et al. |
| 4,405,579 A | 9/1983 | Sartori et al. |
| 4,405,586 A | 9/1983 | Sartori et al. |
| 4,466,915 A | 8/1984 | Lai |
| 4,489,563 A | 12/1984 | Kalina |
| 4,524,587 A | 6/1985 | Kantor |
| 4,525,294 A | 6/1985 | Sartori et al. |
| 4,605,743 A | 8/1986 | Malz et al. |
| 4,643,000 A | 2/1987 | Rheinfelder |
| 4,701,530 A | 10/1987 | Swearingen et al. |
| 4,714,597 A | 12/1987 | Trevino |
| 4,889,938 A | 12/1989 | Kristen et al. |
| 4,941,324 A | 7/1990 | Peterson et al. |
| 5,016,445 A | 5/1991 | Wehr |
| 5,126,189 A | 6/1992 | Tanny et al. |
| 5,186,009 A | 2/1993 | Rockenfeller |
| 5,186,010 A | 2/1993 | Wehr |
| 5,245,070 A | 9/1993 | Nishikawa |
| 5,255,534 A | 10/1993 | Ryan |
| 5,303,565 A | 4/1994 | Pravada |
| 5,390,509 A | 2/1995 | Rockenfeller et al. |
| 5,583,270 A | 12/1996 | Nishiguchi |
| 5,873,260 A | 2/1999 | Linhardt et al. |
| 6,117,963 A | 9/2000 | Boinowitz et al. |
| 6,128,917 A | 10/2000 | Riesch et al. |
| 6,130,347 A | 10/2000 | Julius et al. |
| 6,155,057 A | 12/2000 | Angell et al. |
| 6,165,433 A | 12/2000 | Chakravarti et al. |
| 6,184,433 B1 | 2/2001 | Harada et al. |
| 6,395,948 B1 | 5/2002 | Hope et al. |
| 6,423,282 B1 | 7/2002 | Araki et al. |
| 6,475,370 B2 | 11/2002 | Lehmann et al. |
| 6,672,099 B1 | 1/2004 | Yoshimi et al. |
| 6,680,047 B2 | 1/2004 | Klaveness et al. |
| 6,727,015 B1 | 4/2004 | Putter et al. |
| 7,419,646 B2 | 9/2008 | Cadours et al. |
| 7,435,318 B2 | 10/2008 | Arlt et al. |
| 7,638,636 B2 | 12/2009 | Zhou et al. |
| 7,666,813 B2 | 2/2010 | Hoefer et al. |
| 7,754,053 B2 | 7/2010 | Maase |
| 7,827,820 B2 | 11/2010 | Weimer et al. |
| 7,998,714 B2 | 8/2011 | Gellett et al. |
| 8,069,687 B2 | 12/2011 | Jork et al. |
| 8,167,983 B2 | 5/2012 | Seiler et al. |
| 8,277,615 B2 | 10/2012 | Ruffert et al. |
| 8,318,117 B2 | 11/2012 | Lichtfers et al. |
| 8,357,344 B2 | 1/2013 | Bouillon et al. |
| 8,362,095 B2 | 1/2013 | Schwab et al. |
| 8,382,962 B2 | 2/2013 | Massonne et al. |
| 8,470,079 B2 | 6/2013 | Agar et al. |
| 8,500,867 B2 | 8/2013 | Seiler et al. |
| 8,500,892 B2 | 8/2013 | Seiler et al. |
| 8,506,839 B2 | 8/2013 | Shiflett et al. |
| 8,523,978 B2 | 9/2013 | Rojey et al. |
| 8,603,226 B2 | 12/2013 | Garcia Andarcia et al. |
| 8,609,572 B2 | 12/2013 | Earl et al. |
| 8,623,123 B2 | 1/2014 | Seiler et al. |
| 8,664,460 B2 | 3/2014 | Earle et al. |
| 8,696,928 B2 | 4/2014 | Seiler et al. |
| 8,703,451 B2 | 4/2014 | Haas et al. |
| 8,715,521 B2 | 5/2014 | Shiflett et al. |
| 8,784,537 B2 | 7/2014 | Seiler et al. |
| 8,809,576 B2 | 8/2014 | Schraven et al. |
| 8,932,478 B2 | 1/2015 | Seiler et al. |
| 9,221,007 B2 | 12/2015 | Rolker et al. |
| 9,409,122 B2 | 8/2016 | Qi et al. |
| 9,630,140 B2 | 4/2017 | Willy et al. |
| 9,840,473 B1 | 12/2017 | Wang et al. |
| 9,878,285 B2 | 1/2018 | Schraven et al. |
| 10,105,644 B2 | 10/2018 | Zehnacker et al. |
| 10,138,209 B2 | 11/2018 | Bahlmann et al. |
| 2002/0169071 A1 | 11/2002 | Sauvage et al. |
| 2002/0198100 A1 | 12/2002 | Mehnert et al. |
| 2003/0085156 A1* | 5/2003 | Schoonover ........... C10G 21/06 |
| | | 208/230 |
| 2003/0106680 A1* | 6/2003 | Serpico ................ B01D 53/268 |
| | | 165/166 |
| 2003/0118887 A1* | 6/2003 | Serpico ................ B01D 53/268 |
| | | 524/261 |
| 2004/0016631 A1 | 1/2004 | Madkour |
| 2004/0133058 A1 | 7/2004 | Arlt et al. |
| 2005/0010076 A1 | 1/2005 | Wasserscheid et al. |
| 2005/0070717 A1 | 3/2005 | Wasserscheid et al. |
| 2005/0129598 A1 | 6/2005 | Chinn |
| 2005/0164082 A1 | 7/2005 | Kishi et al. |
| 2005/0202967 A1 | 9/2005 | Hoefer et al. |
| 2005/0245769 A1 | 11/2005 | Kohler et al. |
| 2006/0070919 A1 | 4/2006 | Vallee et al. |
| 2006/0104877 A1 | 5/2006 | Cadours et al. |
| 2006/0128996 A1 | 6/2006 | Vaultier et al. |
| 2006/0150665 A1 | 7/2006 | Weimer et al. |
| 2006/0197053 A1 | 9/2006 | Shiflett et al. |
| 2006/0251961 A1 | 11/2006 | Olbert et al. |
| 2006/0264645 A1 | 11/2006 | Zhou et al. |
| 2007/0004903 A1 | 1/2007 | Hoff et al. |
| 2007/0095645 A1 | 5/2007 | Masse |
| 2007/0142685 A1 | 6/2007 | Elomari et al. |
| 2007/0144186 A1* | 6/2007 | Shiflett .................. C09K 5/047 |
| | | 62/112 |
| 2007/0164462 A1 | 7/2007 | Liu et al. |
| 2007/0264180 A1 | 11/2007 | Carrette et al. |
| 2007/0286783 A1 | 12/2007 | Carrette et al. |
| 2008/0028777 A1 | 2/2008 | Boesmann et al. |
| 2008/0114105 A1 | 5/2008 | Hell et al. |
| 2008/0283383 A1 | 11/2008 | Ruffert et al. |
| 2008/0306319 A1 | 12/2008 | Earle et al. |
| 2009/0029121 A1 | 1/2009 | Hammermann et al. |
| 2009/0029887 A1 | 1/2009 | Schwab et al. |
| 2009/0036334 A1 | 2/2009 | Schwab et al. |
| 2009/0139232 A1 | 6/2009 | Collis |
| 2009/0170734 A1 | 7/2009 | Schwab et al. |
| 2009/0199709 A1 | 8/2009 | Rojey et al. |
| 2009/0211447 A1 | 8/2009 | Lichtfers et al. |
| 2009/0326228 A1 | 12/2009 | Vaultier et al. |
| 2010/0011958 A1 | 1/2010 | Cadours et al. |
| 2010/0016205 A1 | 1/2010 | Schwab |
| 2010/0029519 A1 | 2/2010 | Schwab et al. |
| 2010/0071557 A1 | 3/2010 | Seiler et al. |
| 2010/0084597 A1 | 4/2010 | Schwab et al. |
| 2010/0086983 A1 | 4/2010 | Gellett et al. |
| 2010/0095703 A1 | 4/2010 | Jork et al. |
| 2010/0104490 A1 | 4/2010 | Bouillon et al. |
| 2010/0132551 A1 | 6/2010 | Bouillon et al. |
| 2010/0186590 A1 | 7/2010 | Vorberg et al. |
| 2010/0192770 A1 | 8/2010 | Andarcia |
| 2010/0269528 A1 | 10/2010 | Gerhard et al. |
| 2010/0288126 A1 | 11/2010 | Agar et al. |
| 2010/0300870 A1 | 12/2010 | Massonne et al. |
| 2010/0324318 A1 | 12/2010 | Prakash et al. |
| 2010/0326126 A1 | 12/2010 | Seiler et al. |
| 2011/0000236 A1 | 1/2011 | Seiler et al. |
| 2011/0081287 A1 | 4/2011 | Bouillon et al. |
| 2011/0094381 A1 | 4/2011 | Lichtfers et al. |
| 2011/0118504 A1 | 5/2011 | Haas et al. |
| 2011/0135549 A1 | 6/2011 | Lichtfers et al. |
| 2011/0185901 A1 | 8/2011 | Jacquin et al. |
| 2011/0247494 A1* | 10/2011 | Dinnage ............... B01D 53/1456 |
| | | 95/92 |
| 2011/0256043 A1 | 10/2011 | Blair et al. |
| 2011/0309295 A1 | 12/2011 | Joh et al. |
| 2012/0011886 A1 | 1/2012 | Shiflett et al. |

(56) References Cited

U.S. PATENT DOCUMENTS

| | | | |
|---|---|---|---|
| 2012/0017762 A1 | 1/2012 | Seiler et al. | |
| 2012/0024756 A1 | 2/2012 | Verma et al. | |
| 2012/0080644 A1 | 4/2012 | Seiler et al. | |
| 2012/0117991 A1 | 5/2012 | Rached | |
| 2012/0186993 A1 | 7/2012 | Huang et al. | |
| 2012/0247144 A1 | 10/2012 | Seiler et al. | |
| 2012/0308458 A1 | 12/2012 | Seiler et al. | |
| 2012/0315366 A1 | 12/2012 | Zehnacher et al. | |
| 2013/0011314 A1 | 1/2013 | Porcheron et al. | |
| 2013/0023712 A1 | 1/2013 | Porcheron et al. | |
| 2013/0026073 A1* | 1/2013 | Martinez Palou | C10G 21/18 208/254 R |
| 2013/0031930 A1 | 2/2013 | Seiler et al. | |
| 2013/0031931 A1 | 2/2013 | Seiler et al. | |
| 2013/0118350 A1 | 5/2013 | Rolker et al. | |
| 2013/0133327 A1 | 5/2013 | Milam et al. | |
| 2013/0219949 A1 | 8/2013 | Seiler et al. | |
| 2013/0247758 A1 | 9/2013 | Seiler et al. | |
| 2013/0255287 A1 | 10/2013 | Forkosh | |
| 2013/0255496 A1 | 10/2013 | Zhang et al. | |
| 2013/0263743 A1 | 10/2013 | Seiler et al. | |
| 2013/0319022 A1 | 12/2013 | Becze et al. | |
| 2013/0327084 A1 | 12/2013 | Shiflett et al. | |
| 2014/0005344 A1 | 1/2014 | Rinker et al. | |
| 2014/0079613 A1 | 3/2014 | Andarcia et al. | |
| 2014/0090558 A1 | 4/2014 | Rolker et al. | |
| 2014/0091008 A1 | 4/2014 | Hardacre et al. | |
| 2014/0105801 A1 | 4/2014 | Rolker et al. | |
| 2014/0120016 A1 | 5/2014 | Rolker et al. | |
| 2014/0127103 A1 | 5/2014 | Qi et al. | |
| 2014/0356268 A1 | 12/2014 | Schraven et al. | |
| 2014/0360369 A1 | 12/2014 | Schraven et al. | |
| 2015/0024106 A1 | 1/2015 | Huller et al. | |
| 2015/0024247 A1 | 1/2015 | Lockett et al. | |
| 2015/0125373 A1 | 5/2015 | Willy et al. | |
| 2015/0141315 A1 | 5/2015 | Jin | |
| 2015/0175738 A1 | 6/2015 | Willy et al. | |
| 2015/0175740 A1 | 6/2015 | Willy et al. | |
| 2015/0308720 A1 | 10/2015 | Zehnacker et al. | |
| 2015/0321139 A1 | 11/2015 | Schraven et al. | |
| 2016/0045857 A1 | 2/2016 | Rolker et al. | |
| 2016/0115827 A1 | 4/2016 | Rached | |
| 2016/0153318 A1 | 6/2016 | Busse et al. | |
| 2016/0175766 A1 | 6/2016 | Zehnacker et al. | |
| 2017/0022447 A1 | 1/2017 | Atkins et al. | |
| 2017/0107449 A1 | 4/2017 | Hruschka et al. | |
| 2017/0354922 A1 | 12/2017 | Zehnacker et al. | |
| 2017/0354923 A1 | 12/2017 | Zehnacker et al. | |
| 2017/0354924 A1 | 12/2017 | Irfan et al. | |
| 2017/0355680 A1 | 12/2017 | Wang et al. | |
| 2017/0355681 A1 | 12/2017 | Bahlmann et al. | |
| 2017/0355682 A1 | 12/2017 | Willy et al. | |
| 2018/0134987 A1 | 5/2018 | Fedor et al. | |
| 2018/0134988 A1 | 5/2018 | Fedor et al. | |
| 2018/0148665 A1 | 5/2018 | Goodrich et al. | |
| 2018/0169572 A1 | 6/2018 | Zehnacker et al. | |

FOREIGN PATENT DOCUMENTS

| | | | |
|---|---|---|---|
| CN | 102335545 | | 2/2012 |
| CN | 102335545 A | * | 2/2012 |
| CN | 102031202 | | 5/2012 |
| CN | 105061496 A | | 11/2015 |
| DE | 400 488 | | 8/1924 |
| DE | 633 146 | | 7/1936 |
| DE | 737031 | | 7/1943 |
| DE | 36 23 680 A1 | | 1/1988 |
| DE | 266 799 A1 | | 4/1989 |
| DE | 195 11 709 | | 10/1996 |
| DE | 103 33 546 | | 2/2005 |
| DE | 10 2004 053 167 | | 5/2006 |
| DE | 10 2010 001 070 | | 7/2011 |
| DE | 10 2010 004 779 | | 7/2011 |
| DE | 10 2011 055 859 | | 6/2013 |
| DE | 10 2013 010 035 | | 12/2014 |
| DE | 10 2014 214 670 | | 1/2016 |
| DE | 10 2014 214 674 | | 1/2016 |
| DE | 10 2014 214 682 | | 1/2016 |
| DE | 10 2014 11019 | | 1/2016 |
| DE | 10 2015 212 749 | | 1/2017 |
| DE | 10 2016 210 481 | | 6/2017 |
| DE | 10 2016 204 928 | | 9/2017 |
| DE | 10 2016 204 929 | | 9/2017 |
| DE | 10 2016 204 930 | | 9/2017 |
| DE | 10 2016 204 931 | | 9/2017 |
| DE | 10 2016 204 932 | | 9/2017 |
| DE | 10 2016 204 937 | | 9/2017 |
| EP | 0 033 529 A1 | | 1/1981 |
| EP | 0 047 967 | | 9/1981 |
| EP | 0 079 767 | | 5/1983 |
| EP | 0 187 130 | | 7/1986 |
| EP | 0 193 327 | | 9/1986 |
| EP | 0 302 020 | | 2/1989 |
| EP | 0 558 019 | | 2/1993 |
| EP | 0 791 643 | | 8/1997 |
| EP | 2 636 715 | | 9/2013 |
| EP | 2 940 394 | | 11/2015 |
| FR | 670 497 | | 11/1929 |
| FR | 2 861 084 | | 4/2005 |
| FR | 2 900 841 A1 | | 11/2007 |
| GB | 1 306 853 | | 2/1973 |
| GB | 1 501 195 | | 2/1978 |
| GB | 2 047 681 | | 12/1980 |
| GB | 2 528 494 | | 1/2016 |
| JP | 33-009879 B | | 11/1958 |
| JP | 57-191407 | | 11/1982 |
| JP | 61-129019 | | 6/1986 |
| JP | 62-73055 | | 4/1987 |
| JP | 1-134180 | | 5/1989 |
| JP | H01-198679 | | 8/1989 |
| JP | 2-298767 | | 12/1990 |
| JP | 4-268176 | | 9/1992 |
| JP | 6-307730 | | 11/1994 |
| JP | 7-167521 | | 7/1995 |
| JP | 09 313864 | | 12/1997 |
| JP | 2000-202299 | | 7/2000 |
| JP | 2001-219164 | | 8/2001 |
| JP | 2002-047258 | | 2/2002 |
| JP | 2004-44945 | | 2/2004 |
| JP | 2006-160969 | | 6/2006 |
| JP | 2006-239516 | | 9/2006 |
| JP | 2006-282525 | | 10/2006 |
| JP | 2010-034301 | | 2/2010 |
| JP | 2010-54136 | | 3/2010 |
| JP | 2013-051238 | | 3/2013 |
| JP | 2013-139425 | | 7/2013 |
| JP | 2013-250186 | | 12/2013 |
| RU | 2 101 625 | | 1/1998 |
| RU | 2 122 642 | | 11/1998 |
| RU | 2 183 003 | | 5/2002 |
| WO | WO 93/13367 | | 7/1993 |
| WO | WO 00/61698 A1 | | 10/2000 |
| WO | WO 2002/016671 | | 2/2002 |
| WO | WO 2004/016631 | | 2/2004 |
| WO | WO 2004/082809 | | 9/2004 |
| WO | WO 2006/012097 | | 2/2006 |
| WO | WO 2006/048182 | | 5/2006 |
| WO | WO 2007/099041 | | 9/2007 |
| WO | WO 2007/101397 | | 9/2007 |
| WO | WO 2007/138307 | | 12/2007 |
| WO | WO 2009/032959 | | 3/2009 |
| WO | WO 2009/074535 | | 6/2009 |
| WO | WO 2009/133059 | | 11/2009 |
| WO | WO 2010/037109 | | 4/2010 |
| WO | WO 2010/136783 | | 12/2010 |
| WO | WO 2011/131552 | | 10/2011 |
| WO | WO 2012/082093 | | 6/2012 |
| WO | WO 2012/110987 | | 8/2012 |
| WO | WO 2012/150051 | | 11/2012 |
| WO | WO 2013/041300 | | 3/2013 |
| WO | WO 2013/050230 | | 4/2013 |
| WO | WO 2013/050242 | | 4/2013 |
| WO | WO 2013/072147 | | 5/2013 |

(56) References Cited

FOREIGN PATENT DOCUMENTS

| WO | WO 2015/000637 | 1/2015 |
|---|---|---|
| WO | WO 2015/079262 | 6/2015 |
| WO | WO 2016/005769 | 1/2016 |
| WO | WO 2016/189330 | 12/2016 |
| WO | WO 2016/189333 | 12/2016 |
| WO | WO 2017/005538 | 1/2017 |

OTHER PUBLICATIONS

English language translation of Singaporian Written Opinion for corresponding Singapore application 10201704818Q, filed Jun. 12, 2017.
Kuhlmann, et al., "Imidazolium dialkylphosphates—a class of versatile, halogen-free and hydrolytically stable ionic liquids," *Green Chem.* 9:233-242 (2007).
Li, et al., "Efficient absorption of ammonia with hydroxyl-functionalized ionic liquids," *RCS Adv.* 5:81362-81370 (2015).
Kanakubo, et al., "$CO_2$ solubility in and physical properties for ionic liquid mixtures of 1-butyl-3-methylimidazolium acetate and 1-butyl-3-methylimidazoliumbis(trifluoromethanesulfonyl)amide," *Journal of Molecular Liquids* 217:112-119 (2016); available online Feb. 12, 2016.
Krannich, et al., "Characterization of Six Hygroscopic Ionic Liquids with Regard to Their Suitability for Gas Dehydration: Density, Viscosity, Thermal and Oxidative Stability, Vapor Pressure, Diffusion Coefficient, and Activity Coefficient of Water," *Journal of Chemical Engineering & Data* 61:1162-1176 (Feb. 2016).
Kriebel, et al., "Absorption, 2. Design of Systems and Equipment," Ulmann's Encyclopedia of Industrial Chemistry, vol. 1, pp. 75-90 (2008).
Lall-Ramnarine, et al., "Probing the Physical Properties, Synthesis and Cellulose Dissolution Ability of Dialkyl Phosphate Ionic Liquids," *Phosphorous, Sulfur, and Silicon* 190:891-895 (2015).
Lungwitz, Ralf, "Ionische Flüssigkeiten—Polarität und Wechselwirkungen mit silikatischen Oberflächen," Dissertation Technische Universität Chemnitz (Nov. 2011); with English language translation of relevant parts.
English language translation of Mao, et al., "Development and Application of New Technique for Recovery of Low Partial Pressure Carbon Dioxide," *Journal of Chemical Industry & Engineering* 25(3):12-15 (Jun. 2004).
English language translation of Rolker, et al., "Separation of carbon dioxide from flue gases by means of absorption," *Chemie Ingenieur Tecknik* 78(4):416-424 (Jul. 2006).
OECD Guidelines for the Testing of Chemicals, Test No. 104, items 14-19, (adopted May 1981).
Projekt der Deutschen Bundesstiftung: Gasreinigung mit ionischen Flüssigkeiten Umwelt; Endbericht (Sep. 2009); with English language translation of relavant parts.
English language translation of XIAO, "Study on Technique for Recovery of Carbon Dioxide from Flue Gas," *Modern Chemical Industry* 24(5):47-49 (May 2004).
German Search Report dated Feb. 21, 2017 for counterpart German application DE 10 2016 210 484.5 with partial machine translation.
U.S. Appl. No. 14/124,472, filed Dec. 6, 2013, 2014-0090558 A1, Apr. 3, 2014, Rolker.
U.S. Appl. No. 14/373,350, filed Jul. 19, 2014, 2014-0356268 A1, Dec. 4, 2014, Schraven.
U.S. Appl. No. 14/973,084, filed Dec. 17, 2015, 2016-0175766 A1, Jun. 23, 2016, Zehnacker.
U.S. Appl. No. 15/486,300, filed Apr. 13, 2017, Bahlmann.
U.S. Appl. No. 15/619,561, filed Jun. 12, 2017, Irfan.
U.S. Appl. No. 15/619,566, filed Jun. 12, 2017, Willy.
U.S. Appl. No. 15/619,567, filed Jun. 12, 2017, Wang.
U.S. Appl. No. 15/619,573, filed Jun. 12, 2017, Zehnacker.
U.S. Appl. No. 15/619,584, filed Jun. 12, 2017, Zehnacker.
Blachly, et al., "Stabilization of Monoethanolmine Solutions in Carbon Dioxide Scrubbers," *J. Chem. Eng. Data* 11(3):401-403 (Jul. 1966).
Call, "Aminoxyle—eine Klasse stabiler," *Pharmazie in unserer Zeit* 3:83-95 (Jan. 1977); with English language translation attached.
Kirchhoff, et al., "Triacetoneamine Derivatives Industrial Applications and Recent Developments," pp. 1-9, Addcon World '99 (Two-Day Conference, Oct. 1999).
Lewin, et al., "Molecular Features Associated with Polyamine Modulation of NMDA Receptors," *J. Med. Chem.* 41:988-995 (published online Feb. 1998).
Luo, et al., "Dehumidification performance of [EMIM]$BF_4$," *Applied Thermal Engineering* 31(14-15):2772-2777 (Oct. 2011).
Luo, et al., "Investigation of feasibility of ionic liquids used in solar liquid desiccant air conditioning system," *Solar Energy* 86(9):2781-2724 (Sep. 2012).
Satori, et al., "Sterically Hindered Amines for $CO_2$ Removal from Gases," *Ind. Eng. Chem. Fundam.* 22(2):239-249 (accepted Jan. 1983).
Gerald Scott, Develpoments in polymer stabilization-5, Chapter 3: Antioxidant action of sterically hindered amines and related compounds, Shlyapintokh and Ivanor; pp. 41-70, Applied Science Publishers (1982).
Shao & Stangeland, "Amines Used in $CO_2$ Capture—Health and Environmental Impacts," Bellona Report (Sep. 2009).
Ulmann's Encyclopedia of Industrial Chemistry, 5th Edition, vol. 83, "Antioxidants" pp. 91-104 (1985).
Wellner, et al., "Entwässerung ionischer Flüssigkeiten in einem Fallfilmverdampfer," *Chemie Ingenieur Technik* 83(9):1493-1501(Jul. 2011); with complete English language translation.
Yunus, "Gaslöslichkeit in ionischen Flüssigkeiten," IsoSORP Application Note Nr. 4:1-2 (Feb. 2014); with complete English language translation.
Encylopedia of Chemical Process and Design, Ed. John J. McKetta, vol. 32. Marcel Deckker, Inc. (1990) pp. 123-126.
U.S. Appl. No. 15/742,436, filed Jan. 5, 2018, Zehnacker.
Abelló, et al., "Supported choline hydroxide (ionic liquid) as heterogeneous catalyst for aldol condensation reactions," *Chem. Comm.* 1096-1097 (2004).
Alcade, et al., "A Simple Halide-to-Anion Exchange Method for Heteroaromatic Salts and Ionic Liquids," *Molecules* 17:4007-4027 (2012).
Cole, et al., "Novel Brønsted Acidic Ionic Liquids and Their Use as Dual Solvent—Catalysts," *J. Am. Chem. Soc.* 124:5962-5963 (2002).
Ishiguro, et al., "Structure, solvation, and acid-base property in ionic liquids," *Pure Appl. Chem.* 82(10):1927-1941 (Aug. 2010).
Manic, et al., "Extraction of Free Fatty Acids from Soybean Oil Using Ionic Liquids or Poly(ethyleneglycol)s," *AIChE* 57(5):1344-1355 (May 2011).
Nockemann, et al., "Task-Specific Ionic Liquid for Solubilizing Metal Oxides," *J. Phys.Chem.* 110(42): 20978-20992 (Oct. 2006).
Smiglak, et al., "New hydrogen carbonate precursors for efficient and byproduct-free synthesis of ionic liquids based on 1,2,3,-tirmethylimidazolium and N,N-dimethylpyrrolidinium cores," *Green Chem.* 12:491-501 (2010).
Zhao, et al., "Review: Use of ionic liquids as 'green' solvents for extractions," *J. Chem. Technol. Biotechnol.* 80: 1089-1096 (published online May 2005).
"Mutual Solubility of Water and Pyridine Derivatives" by Richard M. Stephenson, *J. Chem. Eng. Data* 38, p. 428-431, (Jul. 1993).
"Review of Organic Functional Groups: Introduction to Medicinal Organic Chemistry" by Thomas L. Lemke, Lippincott Williams & Wilkins, p. 40 (2003).
"Review of Organic Functional Groups: Introduction to Medicinal Organic Chemistry" by Thomas L. Lemke, Lippincott Williams & Wilkins, p. 39 (2003).
Brennecke, et al., "Ionic Liquids: Innovative Fluids for Chemical Processing," *AIChE Journal* 47(11):2384-2389 (Nov. 2001).
Chua, et al., "Improved Thermodynamic Property Fields of LiBr-$H_2O$ Solution," *International Journal of Refrigeration* 23:412-429 (Sep. 2000).
De Lucas, et al., "Vapor Pressures, Densities, and Viscosities of the (Water + Lithium Bromide + Lithium Formate) System and (Water + Lithium Bromide + Potassium Formate) System," *Journal of Chemical and Engineering Data, American Chemical Society*, US 48(1):18-22 (Jan. 2003).

(56) References Cited

OTHER PUBLICATIONS

De Lucas, et al., "Absorption of Water Vapor into Working Fluids for Absorption Refrigeration Systems," *Industrial & Engineering Chemistry Research, American Chemical Society*, US 46(1):345-350 (2007); (published online Dec. 2006).

Domanska, et al., Solubility of 1-Alkyl-3-ethylimidazolium-Based Ionic Liquids in Water and 1-Octanol, *J. Chem. Eng. Data* 53:1126-1132 (Apr. 2008).

Galán, et al., "Solvent Properties of Functionalized Ionic Liquids for $CO_2$ Absorption," *IChemE* 85(A1):31-39 (Jan. 2007).

Glebov, et al., "Experimental Study of Heat Transfer Additive Influence on the Absorption Chiller Performance," *International Journal of Refrigeration* 25:538-545 (Aug. 2002).

Kim, et al., "Surface tension and viscosity of 1-butyl-3-methylimidazolium iodide and 1-butyl-3-methylimidazolium tetrafluoroborate, and solubility of lithium bromide+1-butyl-3-methylimidazolium bromide in water," *Korean J. Chem. Eng.* 23(1):113-116 (Jan. 2006).

Kim, et al., "Performance Evaluation of Absorption Chiller Using LiBr + $H_2N(CH_2)_2OH$ + $H_2O$, LiBr + $HO(CH_2)_3OH$ + $H_2O$, and LiBr + ($HOCH_2CH_2NH$ + $H_2O$ as Working Fluids," *Applied Thermal Engineering* 19:217-225 (Feb. 1999).

Kim, et al., "Refractive Index and Heat Capacity of 1-Butyl-3-Methylimidazolium Bromide and 1-Butyl-3-Methylimidazolium Tetrafluoroborate, and Vapor Pressure of Binary Systems for 1-Butyl-3-Methylimidazolium Tetrafluoroborate—Trifluoroethanol," *Fluid Phase Equilibria* 218:215-220 (Apr. 2004).

Li, et al., "Correlation and Prediction of the Solubility of $CO_2$ and $H_2S$ in an Aqueous Solution of 2-Piperidineethanol and Sulfolane," *Ind. Eng. Chem. Res.* 37:3098-3104 (May 1998).

Liu, et al., The physical properties of aqueous solution of room-temperature ionic liquids based on imidazolium:Database and Evaluation, *J. Mol. Liquids* 140:68-72 (Jan. 2008).

Mitsubishi Heavy Industries, Ltd., "Flue Gas $CO_2$ Recovery Technology and Its Application to EOR: an Effective Strategy for Addressing the Issues of Global Warming and Peaking Oil Supply," vol. 44, p. 20-23 (2007).

Perez-Blanco, "A Model of an Ammonia-Water Falling Film Absorber," ASHRAE Transactions vol. 94, pp. 467-483, 1988; Presented at the winter meeting in Dallas Texas of the American Society of Heating, Refrigerating and Air-Conditioning Engineers, Inc. (1988).

Wasserscheid, et al., "Ionic Liquids—New "Solutions" for Transition Metal Catalysis," *Angew. Chem. Int. Ed.* 39:3772-3789 (Nov. 2000).

Wu, et al., "Novel Ionic Liquid Thermal Storage for Solar Thermal Electric Power Systems," *Proceeding of Solar Forum. Solar Energy: The Power to Choose* (Apr. 21-25, 2001).

Yoon, et al., "Cycle Analysis of Air-Cooled Absorption Chiller Using a New Working Solution," *Energy* 24:795-809 (Sep. 1999).

Zhang, et al., "Screening of ionic Liquids to Capture CO2 by COSMO-RS and Experiments," *AIChE Journal* 54(10) :2171-2728 (Oct. 2008).

Zhou, The Vapor Surfactant Theory of Absorption and Condensation Enhancement, *Proc. Int. Sorption Heat Pump Conference*, (Sep. 24-27, 2002).

Ziegler, et al., "Heat-Transfer Enhancement by Additives," *International Journal of Refrigeration* 19:301-309 (Jun. 1996).

Ziegler, et al., "Multi-effect absorption chillers," *Rev. Int. Froid* 16(5):301-311 (1993).

Ziegler, et al., "Recent developments and future prospects of sorption heat pump systems," *Int. J. Therm. Sci.* 38:191-208 (Mar. 1999).

Chung, et al., "Dehumidification of Moist Air With Simultaneous Removal of Selected Indoor Pollutants by Triethylene Glycol Solutions in a Packed-Bed Absorber," *Separation Science and Technology* 30(7-9): 1807-1832 (1995).

U.S. Appl. No. 16/300,466, filed Nov. 9, 2018, Wang.

Office Action for U.S. Appl. No. 15/619,573, dated Feb. 14, 2019.

Response to Office Action dated Feb. 14, 2019 for U.S. Appl. No. 15/619,573, filed May 13, 2019.

Office Action for U.S. Appl. No. 14/973,084, dated Nov. 1, 2017. Application is now abandoned. Application was published as US 2016/0175766.

Office Action for U.S. Appl. No. 15/619,566, dated May 29, 2018. Application is now abandoned. Application was published as US 2017/0355682.

Office Action for U.S. Appl. No. 15/619,561, dated Feb. 22, 2019.

Response to Office Action dated Feb. 22, 2019 for U.S. Appl. No. 15/619,561, filed May 14, 2019.

U.S. Appl. No. 15/742,436, filed Jan. 15, 2018, US 2018/0169572 A1, Jun. 21, 2018, Zehnacker.

Notice of Allowance dated Jul. 30, 2019 for copending U.S. Appl. No. 15/619,561.

Notice of Allowance dated Aug. 7, 2019 for copending U.S. Appl. No. 15/619,573.

Notice of Allowance dated Aug. 12, 2019 for copending U.S. Appl. No. 15/742,436.

* cited by examiner

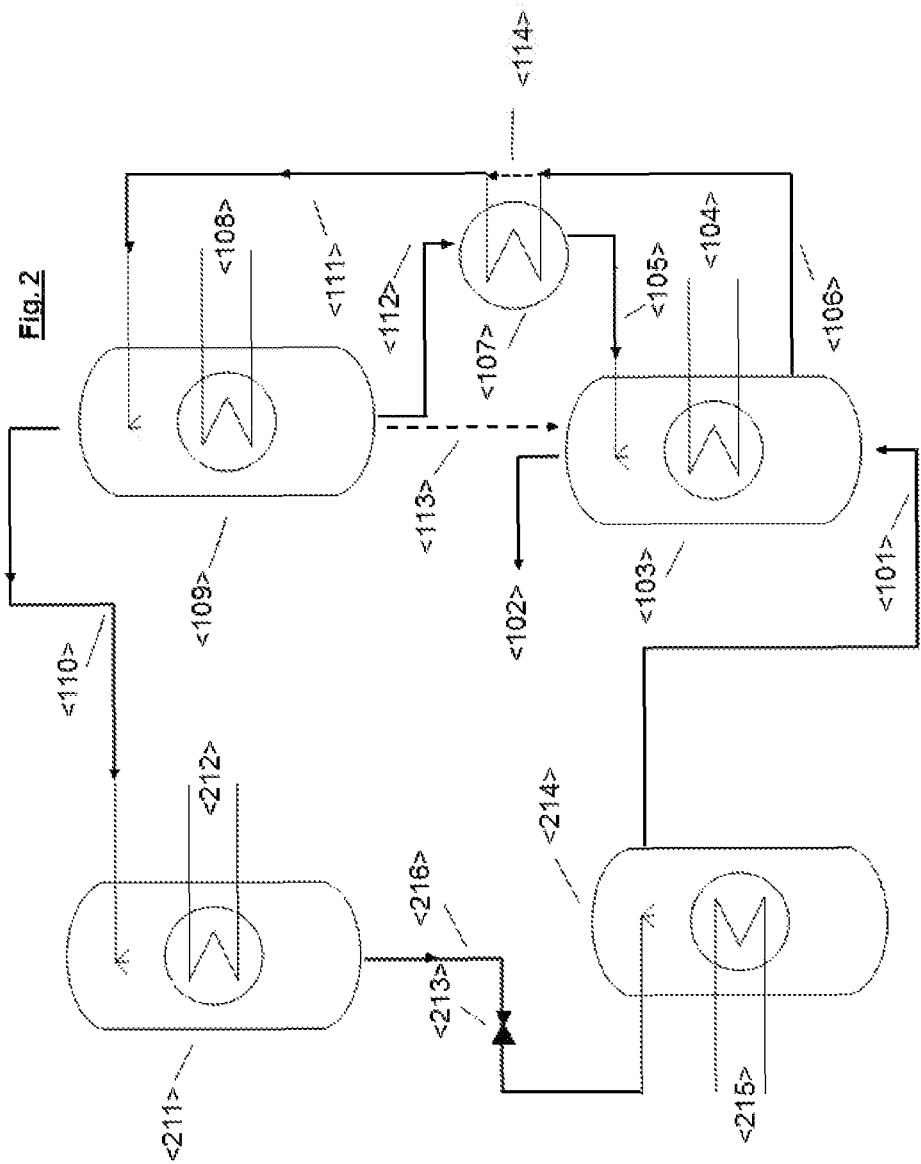

PROCESS FOR DEHUMIDIFYING MOIST GAS MIXTURES

CROSS REFERENCE TO RELATED APPLICATIONS

The present application claims priority under 35 USC § 119 to German application, DE 10 2016 210 484.5, filed on Jun. 14, 2016, the contents of which is incorporated herein by reference in its entirety

FIELD OF THE INVENTION

The invention relates to a process for dehumidifying a moist gas mixture. The invention further relates to an apparatus for dehumidifying a moist gas mixture and to the use of said apparatus in the process according to the invention.

BACKGROUND OF THE INVENTION

Dehumidification of moist gas mixtures is necessary in a multitude of technical fields. For instance, ventilation and air conditioning of buildings or vehicles generally necessitates not only cooling but also dehumidification of the air since the air to be cooled is often so humid that during cooling to the desired temperature the temperature falls below the dew point temperature. Hence in conventional air conditioning systems dehumidification of the air accounts for a large part of the electricity consumption.

The electricity consumption of air conditioning systems for buildings is reduced by dehumidifying the air by adsorption or absorption of water with a drying medium and subsequently regenerating the water-laden drying medium by heating to a temperature at which the water is desorbed again. Compared to adsorption on a solid adsorbent, the advantage of absorption in a liquid absorption medium is that air dehumidification can be carried out with reduced equipment complexity and with less drying medium and that regeneration of the water-laden drying medium using solar heat is easier to carry out.

A further technical field where dehumidifying of moist gas mixtures is employed is the field of absorption chillers (also known as "absorption heat pump", principle described in WO 2014/079675 A1). Here, the moist gas mixture is formed during evaporation of water under low pressure. The water vapour thus formed needs to be removed from the moist gas mixture so that said mixture may then be returned to the water evaporation to pass through a new cycle. Here too, absorption in a liquid absorption medium is favoured over adsorption on a solid adsorption medium.

Finally, dehumidification of moist gas mixtures is important in the field of natural gas extraction, as described in DE 10 2010 004 779 A1.

Examples of the materials typically incorporated in air or natural gas dehumidifying plants and in chillers include titanium, copper and noble metals.

The aqueous solutions of lithium bromide, lithium chloride or calcium chloride hitherto employed as liquid absorption media in commercial air conditioning systems have the disadvantage that they are corrosive towards the metallic materials of construction typically employed in air conditioning systems and that they thus necessitate the use of expensive special materials of construction. This problem is also encountered with steel and stainless steel. These solutions can additionally cause problems due to salt crystallizing out of the absorption medium.

Y. Luo et al., Appl. Thermal Eng. 31 (2011) 2772-2777 proposes using the ionic liquid 1-ethyl-3-methylimidazolium tetrafluoroborate in place of aqueous solutions of lithium bromide for air dehumidification. However, this ionic liquid has the disadvantage of only poor absorption capability.

Y. Luo et al., Solar Energy 86 (2012) 2718-2724 proposes the ionic liquid 1,3-dimethyimidazolium acetate as an alternative to 1-ethyl-3-methylimidazolium tetrafluoroborate for air dehumidification. However, 1,3-dimethyimidazolium acetate is not stable and decomposes to a not inconsiderable extent during desorption.

This problem is also encountered for the ionic liquids proposed in US 2011/0247494 A1, paragraph [0145]. This document proposes using trimethylammonium acetate or 1-ethyl-3-methylimidazolium acetate as liquid drying agent in place of aqueous lithium chloride solution. Example 3 compares water uptake from humid air for a series of further ionic liquids.

CN 102335545 A describes aqueous solutions of ionic liquids that do not suffer from the abovementioned problems as absorption media for air dehumidification. CN 102335545 A chiefly describes steel-based air dehumidifiers. Ionic liquids described are, inter alia, 1,3-dimethyimidazolium dimethyl phosphate, 1-ethyl-3-methylimidazolium dimethyl phosphate and 1-butyl-3-methylimidazolium dimethyl phosphate. The absorption media are reported to be noncorrosive toward steel. However, heat transfer, which is important for efficient air dehumidification, is relatively low with the ionic liquids cited in CN 102335545 A in steel-based apparatuses.

Yet, heat transfer is an important parameter which must be accounted for when choosing absorption media. Thus, in the field of air dehumidification absorption media which ensure a particularly good heat transfer between themselves and further constituents of an air dehumidifier are particularly readily employable. In air dehumidifiers in which metallic components (for example steel) are employed this heat transfer takes place at least partially between the absorption media and metallic surfaces.

The present invention accordingly has for its object the provision of absorption media that ensure better heat transfer than prior art absorption media when used in steel-based air conditioning systems, air dehumidifiers, absorption chillers etc. Absorption media which achieve this object have now surprisingly been found.

BRIEF DESCRIPTION OF THE DRAWINGS

FIG. 2 illustrates an absorption chiller into which an apparatus V2 is integrated.

DETAILED DESCRIPTION OF THE INVENTION

Figure 1:
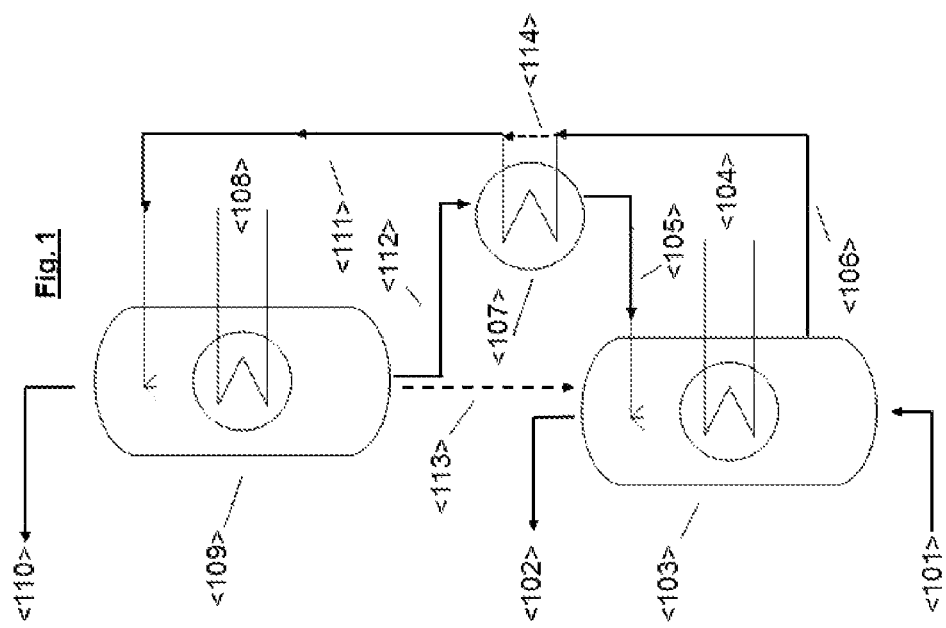
FIG. 1 illustrates an embodiment of the apparatus V2/V1 according to the invention.

The present invention accordingly relates in a first aspect to a process for dehumidifying a moist gas mixture G, in particular moist air, in an apparatus $V_1$, comprising the steps of:

(a) contacting the moist gas mixture G with an aqueous liquid absorption medium $A_{VE}$ comprising a mixture of at least one trialkyl phosphate of structure (I):

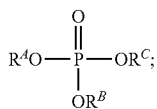

(I)

and at least one salt S selected from the group consisting of $Q^+A^-$, $Q^+(R^1O)_2PO_2^-$, $(Q^+)_2R^2OPO_3^{2-}$, $Q^+M^+R^3OPO_3^{2-}$, wherein $A_{VE}$ at least partially absorbs water from the moist gas mixture G, to afford an aqueous liquid absorption medium $A_{VE1}$ having an elevated water content compared to $A_{VE}$ and a gas mixture $G_1$ having a relatively low water content compared to the moist gas mixture G, (b) partially removing water from $A_{VE1}$ to obtain an aqueous liquid absorption medium $A_{VE2}$ having a relatively low water content compared to $A_{VE1}$, wherein the apparatus $V_1$ at least partially comprises a surface made of a steel material of construction $O_{st}$ and in the apparatus $V_1$ at least one of $A_{VE}$, $A_{VE1}$, $A_{VE2}$ contacts the surface made of a steel material of construction $O_{st}$ via at least one contact surface, characterized in that $Q^+$ is a dialkylimidazolium cation in which in particular the alkyl groups each independently of one another have 1 to 10 carbon atoms, wherein $A^-$ is an anion selected from the group consisting of $R^*COO^-$, $R'SO_3^-$, $HSO_4^-$, $R''SO_4^-$, wherein $R^*$, $R'$, $R''$, $R^A$, $R^B$, $R^C$, $R^1$, $R^2$, $R^3$ are each independently of one another an alkyl group, in particular having 1 to 10, preferably 1 to 8, more preferably 1 to 6, yet more preferably 1 to 4, still more preferably 1 to 2, carbon atoms and wherein $M^+$ is an alkali metal ion, preferably $Li^+$, $K^+$ or $Na^+$, yet more preferably $K^+$ or $Na^+$.

The moist gas mixture G employed in the process is not particularly restricted.

"Moist" is to be understood as meaning in the context of the invention "comprising water, in particular water vapour".

"Aqueous" is to be understood as meaning that the particular solution (i.e. in the case of the aqueous liquid absorption media said absorption media) comprises water.

"Dehumidifying" is to be understood as meaning at least partially removing water.

"At least partially" is to be understood as meaning in the context of the invention "partially or completely".

"Moist gas mixture G" is accordingly to be understood as meaning in the context of the invention that the gas mixture G comprises water, preferably water vapour ("water vapour" is to be understood as meaning water in the gaseous physical state), and that its composition is otherwise not particularly restricted. The water content of this moist gas mixture is not particularly restricted and is in particular from 0.01 vol %-99.99 vol % ("vol %" indicates the volume of water vapour based on the overall volume of moist gas mixture G). The composition of the moist gas G may otherwise vary depending on the application of the process according to the invention. The moist gas mixture G is in particular selected from moist natural gas, moist air (this may be moist indoor air or the moist air resulting from evaporation of water in absorption chillers), preferably moist air. For moist natural gas the water content is in particular from 0.01 vol % to 15.00 vol %, for moist air said content is in particular from 0.01 vol % to 15.00 vol % in the case of moist indoor air or in particular from 95.00 vol % to 99.99 vol % which is the preferred range when moist air resulting from evaporation of water in absorption chillers is concerned.

The process according to the invention is carried out in an apparatus $V_1$ which at least partially comprises a surface made of a steel material of construction $O_{st}$ (in the context of the invention $O_{st}$ is short for "surface made of a steel material of construction") and in which at least one of the aqueous liquid absorption media selected from the group consisting of $A_{VE}$, $A_{VE1}$, $A_{VE2}$ contacts the surface made of a steel material of construction $O_{st}$ via at least one contact surface.

In particular, an apparatus $V_1$ having the following components may be employed:

(i) at least one water absorption unit $W_{abs1}$ set up for contacting the moist gas mixture with the aqueous liquid absorption medium $A_{VE}$, (ii) at least one water desorption unit $W_{des1}$ which comprises a heat exchanger $W_{x1}$ and is set up for at least partially removing water from an aqueous liquid absorption medium $A_{VE}$, (iii) and a circuit $U_1$ which connects the water absorption unit $W_{abs1}$ with the water desorption unit $W_{des1}$ and by means of which the aqueous liquid absorption medium $A_{VE}$ may be circulated.

The water absorption unit $W_{abs1}$ is the component in which step a) of the process according to the invention in particular is carried out. Employable water absorption units $W_{abs1}$ include in particular the water absorbers known to those skilled in the art. Said absorbers are based on the principle of increasing the surface area of the aqueous liquid absorption medium $A_{VE}$ and simultaneously achieving the longest possible residence time of the aqueous liquid absorption medium $A_{VE}$ in the water absorber during absorption of water. It is in particular possible here to employ water absorbers selected from the group of: packed beds, spray columns, falling-films, bubble columns, tray columns, wet scrubbers (for example Venturi scrubbers), stirred tanks and combinations of these absorbers. It is particularly preferable to employ falling-films, in particular shell and tube falling-films, as water absorbers. The water absorption unit $W_{abs1}$ may in particular also comprise an additional heat exchanger $W_{z1}$ set up such that the aqueous liquid absorption medium $A_{VE}$ is coolable.

The water desorption unit $W_{des1}$ which comprises a heat exchanger $W_{x1}$ is the unit in which step b) of the process according to the invention in particular is carried out. The water desorption unit $W_{des1}$ is based on the principle of supplying heat to the water-laden liquid absorption medium $A_{VE}$ (in particular $A_{VE1}$), increasing the surface area of the water-laden liquid absorption medium $A_{VE}$ (in particular $A_{VE1}$) and simultaneously achieving the longest possible residence time of the water-laden liquid absorption medium $A_{VE}$ (in particular $A_{VE1}$) in the water desorption unit.

Employable water desorption units $W_{des1}$ comprising a heat exchanger $W_{x1}$ include in particular the combinations of heat exchanger and water desorber known to those skilled in the art, in particular horizontal tube evaporators having an upstream heat exchanger, in particular shell and tube heat exchangers, plate and frame heat exchangers. In addition the water desorption unit $W_{des1}$ comprising a heat exchanger $W_{x1}$ may also be a water desorber having an integrated heat exchanger. Such water desorbers having an integrated heat exchanger are in particular climbing film evaporators, long tube vertical evaporators, short tube vertical evaporators, forced circulation evaporators, agitated thin film evaporators. It is particularly preferable to employ falling-films, in particular shell and tube falling-films, as water desorption unit $W_{des1}$.

Circuit $U_1$ in particular passes $A_{VE1}$ from step a) of the process according to the invention from the water absorption unit $W_{abs1}$ to the water desorption unit $W_{des1}$ and more preferably—in particular when the process according to the invention is carried out in continuous fashion—additionally passes $A_{VE2}$ from step b) of the process according to the invention from the water desorption unit $W_{des1}$ to the water desorption unit $W_{abs1}$.

The circuit $U_1$ is in particular a conduit, in particular selected from the group consisting of tube, hose.

In a further preferred embodiment the circuit $U_1$ also comprises a pump.

A first step of the process according to the invention comprises contacting the moist gas mixture G with an aqueous liquid absorption medium $A_{VE}$ comprising a mixture of at least one trialkyl phosphate of structure (I):

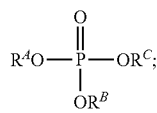
(I)

and at least one salt S selected from the group consisting of $Q^+A^-$, $Q^+(R^1O)_2PO_2^-$, $(Q^+)_2R^2OPO_3^{2-}$, $Q^+M^+R^3OPO_3^{2-}$. The contacting may be effected in any way known to those skilled in the art, in particular in a water absorption unit $W_{abs1}$. The contacting causes the absorption medium $A_{VE}$ to at least partially absorb moisture, i.e. water, from the moist gas stream G to afford an aqueous liquid absorption medium $A_{VE1}$ having an elevated water content compared to the aqueous liquid absorption medium $A_{VE}$ and a gas mixture $G_1$ having a relatively low water content compared to the moist gas mixture G.

It is preferable to cool the absorption medium $A_{VE}$ during contacting of the moist gas mixture G in order that as much moisture as possible is absorbed from the moist gas mixture G. This may be achieved, for example, via an additional heat exchanger $W_{zj}$ in the water absorption unit $W_{abs1}$. The temperature of the absorption medium $A_{VE}$ during contacting of the moist gas mixture G is thus preferably in the range from 2° C. to 100° C., preferably 3° C. to 80° C., more preferably 4° C. to 50° C., yet more preferably 5° C. to 30° C.

The absorption medium $A_{VE}$ comprises water and a mixture of at least one trialkyl phosphate of structure (I):

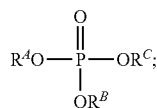
(I)

and at least one salt S selected from the group consisting of $Q^+A^-$, $Q^+(R^1O)_2PO_2^-$, $(Q^+)_2R^2OPO_3^{2-}$, $Q^+M+R^3OPO_3^{2-}$, wherein $Q^+$ is a 1,3-dialkylimidazolium cation in which in particular the alkyl groups each independently of one another have 1 to 10 carbon atoms,
wherein $A^-$ is an anion selected from the group consisting of $R^*COO^-$, $R'SO_3_-$, $HSO_4^-$, $R''SO_4^-$, wherein $R^*$, R', R'', $R^A$, $R^B$, $R^C$, $R^1$, $R^2$, $R^3$ are each independently of one another an alkyl group, in particular having 1 to 10 carbon atoms,
and wherein $M^+$ is an alkali metal ion, preferably $Li^+$, $K^+$ or $Na^+$, yet more preferably $K^+$ or $Na^+$.

In a preferred embodiment of the process according to the invention the salt S is selected from the group consisting of $Q^+A^-$, $Q^+(R^1O)_2PO_2^-$, and $Q^+$ is a dialkylimidazolium cation in which the alkyl groups each independently of one another have 1 to 6, preferably 1 or 4, more preferably 1 or 2 carbon atoms, and $A^-$ is an anion selected from the group consisting of $R^*COO^-$, $R'SO_3^-$, $R''SO_4^-$, wherein $R^*$, $R^1$, R', R'', $R^A$, $R^B$, $R^C$ are each independently of one another an alkyl group having 1 to 6, preferably 1 to 4, more preferably 1 or 2, carbon atoms.

In a more preferred embodiment of the process according to the invention, the salt S has the general formula $Q^+(R^1O)_2PO_2^-$, and $Q^+$ is a dialkylimidazolium cation in which the alkyl groups are each independently of one another methyl or ethyl, and $R^1$, $R^A$, $R^B$, $R^C$ are each independently of one another methyl or ethyl.

In a yet more preferred embodiment of the process according to the invention, the salt S has the general formula $Q^+(R^1O)_2PO_2^-$, and $Q^+$ is selected from the group consisting of 1,3-dimethylimidazolium, 1,3-diethylimidazolium, 1-ethyl-3-methylimidazolium; $R^A$, $R^B$, $R^C$, $R^1$ is methyl or ethyl.

It is moreover particularly preferable in all of the aforementioned embodiments of the process according to the invention when $R^A$, $R^B$, $R^C$ are independently of one another selected from methyl, ethyl; yet more preferably $R^A=R^B=R^C$=methyl or $R^A=R^B=R^C$=ethyl; particularly preferably $R^A=R^B=R^C$=ethyl.

This is because it has been found that, surprisingly, imidazolium salts having at least one ethyl group have a particularly small contact angle and thus ensure particularly good surface wetting. This results in a relatively large contact area, thus also in fewer nonwetted spaces and thus in improved heat transfer inside the apparatus $V_1$ and thus also in a particularly efficient process.

The liquid absorption medium $A_{VE}$ is aqueous, i.e. it comprises water and is thus an aqueous solution.

In particular, in the aqueous liquid absorption medium $A_{VE}$ the total weight of all trialkyl phosphates of structure (I) and all salts S is in the range from 65 wt % to 95 wt % based on the total weight of the aqueous solution. Yet more preferably the total weight of all trialkyl phosphates of structure (I) and all salts S in $A_{VE}$ is in the range from 70 wt % to 90 wt % based on the total weight of the aqueous solution, yet more preferably in the range from 75 wt % to 87 wt %.

In the process according to the invention the ratio of all trialkyl phosphates of structure (I) to the salts S in the absorption medium $A_{VE}$ is not further restricted. However, it is preferable to employ in the process according to the invention an absorption medium $A_{VE}$ in which the ratio of the total weight of all trialkyl phosphates of structure (I) to the total weight of all salts S is in the range 1:9999 to 1:9, more preferably 1:9999 to 1:99, yet more preferably 1:9999 to 1:999.

The gas mixture $G_1$ obtained in the first step of the process according to the invention and having a relatively low water content compared to the moist gas mixture G then represents the dehumidified gas stream which, depending on the application, can be returned to living or working spaces in the form of dehumidified air or in the case of natural gas can be supplied to power generation.

The aqueous liquid absorption medium $A_{VE1}$ obtained in the first step of the process according to the invention has an elevated water content compared to the aqueous liquid absorption medium $A_{VE}$. It will be appreciated that in terms of the trialkyl phosphates of structure (I) comprised by it and the salts S comprised by it, $A_{VE1}$ is identical to $A_{VE}$ and is preferably distinguished therefrom only by its water content.

The second step of the process according to the invention then comprises partially removing water from the aqueous liquid absorption medium $A_{VE1}$ to obtain an aqueous liquid absorption medium $A_{VE2}$ having a relatively low water content compared to the aqueous liquid absorption medium $A_{VE1}$.

This in particular comprises additionally supplying heat to the aqueous liquid absorption medium $A_{VE1}$. The supply of heat and the at least partial removal may be effected in any way known to those skilled in the art, in particular in a water desorption unit $W_{des1}$ comprising a heat exchanger $W_{x1}$. The partial removal of water from the aqueous liquid absorption medium $A_{VE1}$ affords an aqueous liquid absorption medium $A_{VE2}$ having a relatively low water content compared to the aqueous liquid absorption medium $A_{VE1}$.

It will be appreciated that in terms of the trialkyl phosphates of structure (I) comprised by it and the salts S comprised by it the aqueous liquid absorption medium $A_{VE2}$ is identical to $A_{VE1}$ and is preferably distinguished therefrom only by its water content.

It is an essential feature of the process according to the invention that the apparatus $V_1$ at least partially comprises a surface made of a steel material of construction $O_{st}$ (in the context of the invention $O_{st}$ is short for "surface made of a steel material of construction").

A "steel material of construction" in the context of the present invention is to be understood as meaning in particular any iron alloy where the mass fraction of iron is greater than the mass fraction of every other element present. The proportion of iron in the steel material of construction is preferably >50 wt %, more preferably ≥60 wt %, yet more preferably ≥70 wt %, yet more preferably ≥80 wt %, yet more preferably ≥99 wt %.

In accordance with the invention in addition to iron the steel material of construction comprises in particular at least one alloying metal selected from the group consisting of nickel, chromium, vanadium, molybdenum, niobium, tungsten, cobalt, magnesium, manganese, silicon, zinc, lead, copper, titanium, more preferably selected from the group consisting of nickel, chromium, vanadium, molybdenum, niobium, tungsten, cobalt, magnesium, manganese, titanium, particularly chromium, wherein this yet more preferably has a mass fraction in the steel material of construction greater than 10.5 wt % but smaller than 50 wt %.

It is yet more preferable when at the same time the carbon content in the steel material of construction is then always <2.06 wt %, yet more preferably ≤1.2 wt %.

It will be appreciated that the sum of the contents of iron, alloying metal (for example chromium) and carbon in the steel material of construction must not exceed 100 wt %.

The steel material of construction may in particular be in the form of a wrought alloy or of a cast alloy.

It is a further essential feature of the process according to the invention that in the apparatus $V_1$ at least one of the aqueous liquid absorption media selected from the group consisting of $A_{VE}$, $A_{VE1}$, $A_{VE2}$ contacts the surface made of a steel material of construction $O_{st}$ via at least one contact surface. This means that the particular aqueous liquid absorption medium $A_{VE}$, $A_{VE1}$ or $A_{VE2}$ is in direct contact with the surface made of a steel material of construction $O_{st}$ at this contact surface. In the context of the present invention "in direct contact" is to be understood as meaning in particular "wetting". It will be appreciated that the aqueous liquid absorption medium selected from the group consisting of $A_{VE}$, $A_{VE1}$, $A_{VE2}$ and the steel material of construction comprised in the contact surface are thus in direct contact. This is because it has been found that, surprisingly, the contact angle of the absorption media according to the invention are particularly small and thus ensure particularly good heat transfer in the case where said media are aqueous.

In the embodiment according to the invention in which an apparatus $V_1$ is employed and comprises the following components:
 (i) at least one water absorption unit $W_{abs1}$ set up for contacting the moist gas mixture with the aqueous liquid absorption medium $A_{VE}$,
 (ii) at least one water desorption unit $W_{des1}$ which comprises a heat exchanger $W_{x1}$ and is set up for at least partially removing water from an aqueous liquid absorption medium $A_{VE}$,
 (iii) and a circuit $U_1$ which connects the water absorption unit $W_{abs1}$ with the water desorption unit $W_{des1}$ and by means of which the aqueous liquid absorption medium $A_{VE}$ may be circulated,
the contact surface at which the aqueous liquid absorption medium selected from the group consisting of $A_{VE}$, $A_{VE1}$, $A_{VE2}$ contacts the surface made of a steel material of construction $O_{st}$ is disposed in particular in at least one of the components selected from the group water absorption unit $W_{abs1}$, water desorption unit $W_{des1}$, circuit $U_1$, preferably in at least one of the components selected from the group water absorption unit $W_{abs1}$, water desorption unit $W_{des1}$.

This is because it has been found that, surprisingly, the mixtures of at least one trialkyl phosphate of structure (I) and at least one salt S according to the invention show particularly good wetting of steel materials of construction, thus ensure particularly good heat transfer and are thus particularly suitable as absorption media in the apparatus $V_1$ having a surface made of a steel material of construction $O_{st}$ in which one of the aqueous liquid absorption media selected from the group consisting of $A_{VE}$, $A_{VE1}$, $A_{VE2}$ is in direct contact with the surface made of a steel material of construction $O_{st}$.

In a further preferred embodiment the process according to the invention is carried out in continuous fashion. This is to be understood as meaning in particular that following step b) the steps a) and b) are performed at least one more time and that the aqueous liquid absorption medium $A_{VE}$ employed in the steps a) additionally performed in each case is at least partially the aqueous liquid absorption medium $A_{VE2}$ obtained from the step b) performed immediately beforehand, i.e. in particular the water content of the aqueous liquid absorption medium $A_{VE}$ employed in the step a) additionally performed in each case and of the aqueous liquid absorption medium $A_{VE2}$ from the immediately preceding step b) is identical.

It is yet more preferable when this embodiment comprises heating aqueous liquid absorption medium $A_{VE1}$ with heat from aqueous liquid absorption medium $A_{VE2}$. This may be carried out in an additional heat exchanger $W_{y1}$, in particular selected from the group consisting of shell and tube heat exchangers and plate and frame heat exchangers. This makes it possible to carry out the process according to the invention in a particularly energy efficient fashion.

The invention also relates in a further aspect to an apparatus $V_2$ for dehumidifying a moist gas mixture, in particular moist air, comprising the components
(i) an aqueous liquid absorption medium $A_{VO}$ which comprises a mixture of at least one trialkyl phosphate of structure (I):

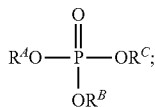
(I)

and at least one salt S selected from the group consisting of $Q^+A^-$, $Q^+(R^1O)_2PO_2^-$, $(Q^+)_2R^2OPO_3^{2-}$, $Q^+M^+R^3OPO_3^{2-}$,
(ii) at least one water absorption unit $W_{abs2}$ set up for contacting the moist gas mixture with the aqueous liquid absorption medium $A_{VO}$,
(iii) at least one water desorption unit $W_{des2}$ which comprises a heat exchanger $W_{x2}$ and is set up for at least partially removing water from an aqueous liquid absorption medium $A_{VO}$,
(iv) and a circuit $U_2$ which connects the water absorption unit $W_{abs2}$ with the water desorption unit $W_{des2}$ and by means of which the aqueous liquid absorption medium $A_{VO}$ may be circulated,
wherein at least one of the components water absorption unit $W_{abs2}$, water desorption unit $W_{des2}$, circuit $U_2$ at least partially comprises a surface made of a steel material of construction $O_{st}$, and
wherein disposed in the apparatus $V_2$ is at least one contact surface at which the aqueous liquid absorption medium $A_{VO}$ contacts the surface made of a steel material of construction $O_{st}$, characterized in that
$Q^+$ is a dialkylimidazolium cation in which in particular the alkyl groups each independently of one another have 1 to 10 carbon atoms,
wherein $A^-$ is an anion selected from the group consisting of $R^*COO^-$, $R'SO_3^-$, $HSO_4^-$, $R''SO_4^-$,
wherein $R^*$, $R'$, $R''$, $R^A$, $R^B$, $R^C$, $R^1$, $R^2$, $R^3$ are each independently of one another an alkyl group, in particular having 1 to 10, preferably 1 to 8, more preferably 1 to 6, yet more preferably 1 to 4, still more preferably 1 to 2, carbon atoms
and wherein $M^+$ is an alkali metal ion, preferably $Li^+$, $K^+$ or $Na^+$, yet more preferably $K^+$ or $Na^+$.

The apparatus $V_2$ according to the invention is suitable for dehumidifying a moist gas mixture, in particular moist air. Said apparatus comprises the following components:

As the first component, the apparatus $V_2$ according to the invention comprises an aqueous liquid absorption medium $A_{VO}$, which comprises a mixture of at least one trialkyl phosphate of structure (I):

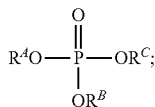
(I)

and at least one salt S selected from the group consisting of $Q^+A^-$, $Q^+(R^1O)_2PO_2^-$, $(Q^+)_2R^2OPO_3^{2-}$, $Q^+M^+R^3OPO_3^{2-}$, wherein $Q^+$ is a dialkylimidazolium cation in which in particular the alkyl groups each independently of one another have 1 to 10 carbon atoms,
wherein $A^-$ is an anion selected from the group consisting of $R^*COO^-$, $R'SO_3^-$, $HSO_4^-$, $R''SO_4^-$,
wherein $R^*$, $R'$, $R''$, $R^A$, $R^B$, $R^C$, $R^1$, $R^2$, $R^3$ are each independently of one another an alkyl group, in particular having 1 to 10 carbon atoms,
and wherein $M^+$ is an alkali metal ion, preferably $Li^+$, $K^+$ or $Na^+$, yet more preferably $K^+$ or $Na^+$.

In a preferred embodiment of the apparatus $V_2$ according to the invention in the absorption medium $A_{VO}$ the salt S is selected from the group consisting of $Q^+A^-$, $Q^+(R^1O)_2PO_2^-$, and $Q^+$ is a dialkylimidazolium cation in which the alkyl groups each independently of one another have 1 to 6, preferably 1 or 4, more preferably 1 or 2 carbon atoms, and $A^-$ is an anion selected from the group consisting of $R^*COO^-$, $R'SO_3^-$, $R''SO_4^-$, wherein $R^*$, $R^1$, $R'$, $R''$, $R^A$, $R^B$, $R^C$ are each independently of one another an alkyl group having 1 to 6, preferably 1 to 4, more preferably 1 or 2, carbon atoms.

In a more preferred embodiment of the apparatus $V_2$ according to the invention in the absorption medium $A_{VO}$ the salt S has the general formula $Q^+(R^1O)_2PO_2^-$, and $Q^+$ is a dialkylimidazolium cation in which the alkyl groups are each independently of one another methyl or ethyl, and $R^1$, $R^A$, $R^B$, $R^C$ are each independently of one another methyl or ethyl.

In a yet more preferred embodiment of the apparatus $V_2$ according to the invention in the absorption medium $A_{VO}$ the salt S has the general formula $Q^+(R^1O)_2PO_2^-$, and $Q^+$ is selected from the group consisting of 1,3-dimethylimidazolium, 1,3-diethylimidazolium, 1-ethyl-3-methylimidazolium; $R^A$, $R^B$, $R^C$, $R^1$ is methyl or ethyl.

It is moreover particularly preferable in all of the aforementioned embodiments of the apparatus $V_2$ according to the invention when in the absorption medium $A_{VO}$ $R^A$, $R^B$, $R^C$ are independently of one another selected from methyl, ethyl; yet more preferably $R^A=R^B=R^C=$methyl or $R^A=R^B=R^C=$ethyl; particularly preferably $R^A=R^B=R^C=$ethyl.

This is because it has been found that, surprisingly, imidazolium salts where R=ethyl group have a particularly small contact angle and thus ensure particularly good surface wetting. This results in a relatively large contact area, thus also in fewer nonwetted spaces and thus in improved heat transfer inside the apparatus $V_2$.

The liquid absorption medium $A_{VO}$ is aqueous, i.e. it comprises water and is thus an aqueous solution.

In particular, in the apparatus $V_2$ according to the invention in the aqueous liquid absorption medium $A_{VO}$ the total weight of all trialkyl phosphates of structure (I) and all salts S is in the range from 65 wt % to 95 wt % based on the total weight of the aqueous solution. Yet more preferably the total weight of all trialkyl phosphates of structure (I) and all salts S in $A_{VO}$ is in the range 70 wt % to 90 wt % based on the total weight of the aqueous solution, yet more preferably in the range 75 wt % to 87 wt %.

In the apparatus $V_2$ according to the invention the ratio of all trialkyl phosphates of structure (I) to the salts S in the absorption medium $A_{VO}$ is not further restricted. However, it is preferable to employ in the apparatus $V_2$ according to the invention an absorption medium $A_{VO}$ in which the ratio of the total weight of all trialkyl phosphates of structure (I) to the total weight of all salts S is in the range 1:9999 to 1:9, more preferably 1:9999 to 1:99, yet more preferably 1:9999 to 1:999.

As a second component the apparatus $V_2$ according to the invention comprises a water absorption unit $W_{abs2}$ set up for contacting the moist gas mixture with the aqueous liquid absorption medium $A_{VO}$. The water absorption unit $W_{abs2}$ may in particular comprise an additional heat exchanger $W_{z2}$ set up such that the aqueous liquid absorption medium $A_{VO}$ is coolable. Employable water absorption units $W_{abs2}$ of this kind include in particular the water absorbers known to those skilled in the art. Said absorbers are based on the principle of increasing the surface area of the aqueous liquid absorption medium $A_{VO}$ and simultaneously achieving the longest possible residence time of the aqueous liquid absorption medium $A_{VO}$ in the water absorber during absorption of water. It is in particular possible here to employ water absorbers selected from the group of: packed beds, spray columns, falling-films, bubble columns, tray columns, wet scrubbers (for example Venturi scrubbers), stirred tanks and combinations of these absorbers. It is particularly preferable to employ falling-films, in particular shell and tube falling-films, as water absorbers.

As a third component the apparatus $V_2$ according to the invention comprises a water desorption unit $W_{des2}$ which comprises a heat exchanger $W_{x2}$ and is set up for at least partially removing water from the aqueous liquid absorption medium $A_{VO}$. Particularly the combinations of heat exchanger and water desorber known to those skilled in the art may be employed therefor. The water desorption unit $W_{des2}$ is based on the principle of supplying heat to the aqueous liquid absorption medium $A_{VO}$, increasing the surface area of the aqueous liquid absorption medium $A_{VO}$ and simultaneously achieving the longest possible residence time of the aqueous liquid absorption medium $A_{VO}$ in the water desorption unit.

Employable water desorption units $W_{des2}$ comprising a heat exchanger $W_{x2}$ include in particular the combinations of heat exchanger and water desorber known to those skilled in the art, in particular horizontal tube evaporators having an upstream heat exchanger, in particular shell and tube heat exchangers, plate and frame heat exchangers. In addition the water desorption unit $W_{des2}$ comprising a heat exchanger $W_{x2}$ may also be a water desorber having an integrated heat exchanger. Such water desorbers having an integrated heat exchanger are in particular climbing film evaporators, long tube vertical evaporators, short tube vertical evaporators, forced circulation evaporators, agitated thin film evaporators. It is particularly preferable to employ as water desorption unit $W_{des2}$ falling-films, in particular shell and tube falling-films.

As a fourth component the apparatus $V_2$ according to the invention comprises a circuit $U_2$ which connects the water absorption unit $W_{abs2}$ with the water desorption unit $W_{des2}$ and by means of which the aqueous liquid absorption medium $A_{VO}$ may be circulated. The circuit $U_2$ is preferably a conduit, yet more preferably selected from the group consisting of tube, hose. In a further preferred embodiment the circuit $U_2$ also comprises a pump.

It is an essential feature of the apparatus $V_2$ according to the invention that said apparatus at least partially comprises a surface made of a steel material of construction $O_{st}$ (in the context of the invention $O_{st}$ is short for "surface made of a steel material of construction").

It is a further essential feature of the apparatus $V_2$ according to the invention that disposed in said apparatus is a contact surface at which the aqueous liquid absorption medium $A_{VO}$ contacts the surface made of a steel material of construction $O_{st}$. This is to be understood as meaning that at this contact surface the aqueous liquid absorption medium $A_{VO}$ is in direct contact with the surface made of a steel material of construction $O_{st}$. In the context of the present invention "in direct contact" is to be understood as meaning in particular "wetting". It will be appreciated that the aqueous liquid absorption medium $A_{VO}$ and the steel material of construction comprised in the contact surface are thus in direct contact.

In a preferred embodiment the apparatus $V_2$ comprises a further heat exchanger $W_{y2}$ (additional to the heat exchanger $W_{x2}$ comprised in the water desorption unit $W_{des2}$). The heat exchanger $W_{y2}$ is set up such that aqueous liquid absorption medium $A_{VO}$ sent from the water absorption unit $W_{abs2}$ to the water desorption unit $W_{des2}$ is suppliable with heat from aqueous liquid absorption medium $A_{VO}$, said medium being conducted away from the water desorption unit $W_{des2}$. This can be ensured in particular by employing as heat exchanger $W_{y2}$ in particular a heat exchanger selected from shell and tube heat exchangers, plate and frame heat exchangers.

In a further preferred embodiment the apparatus $V_2$ is part of an absorption heat pump. This absorption heat pump then comprises as further components a condenser, an evaporator and a coolant, wherein the coolant is water.

The condenser is in particular connected to the water desorption unit $W_{des2}$ via a conduit and is set up for condensing water at least partially removed from the aqueous liquid absorption medium $A_{VO}$ in the water desorption unit $W_{des2}$. The condenser preferably also comprises a cooling water circuit.

The evaporator is in particular connected to the condenser via a conduit (which may comprise a throttling means) and connected to the water absorption unit $W_{abs2}$ via a further conduit and is set up for evaporating condensed water from the condenser. The evaporator preferably also comprises a pressure of <1 bar, more preferably <0.1 bar, to permit evaporation of the condensed water at the lowest possible temperatures. The evaporator may further preferably additionally comprise an apparatus from which heat may be drawn and so that the condensed water may be evaporated (for example a coolant conduit in which coolant is passed into the space in which water is evaporated).

The FIGS. 1 and 2 elucidated hereinbelow show preferred embodiments of the process according to the invention and the apparatus according to the invention.

FIG. 1 (abbreviated to "FIG. 1") shows an embodiment of the apparatus $V_2/V_1$ according to the invention.

The apparatus $V_2$ shown in FIG. 1 comprises a water absorption unit $W_{abs2}$ <103> (with optional additional heat exchanger $W_{z2}$ <104>) to which a conduit <101> leads and from which a conduit <102> leads away, a water desorption unit $W_{des2}$ which comprises a heat exchanger $W_{x2}$ <108> and a water desorber <109> and to which conduit <111> leads and from which conduits <110>, <112> and <113> lead away, and a circuit $U_2$ formed from conduits <106>, <111> and <113> or <106>, <111>, <112> and <105> (in each case optionally with conduit <114>). The apparatus in FIG. 1 may also optionally comprise a further heat exchanger $W_{y2}$ <107> to which conduits <106> and <112> lead and from which conduits <105> and <111> lead away. In addition the apparatus $V_2$ also comprises an aqueous liquid absorption medium $A_{VO}$. Said medium is disposed in one or more of the abovementioned components water absorption unit $W_{abs2}$, water desorption unit $W_{des2}$, circuit $U_2$. Water absorption unit $W_{abs2}$ <103> may optionally also comprise an additional heat exchanger $W_{z2}$ <104>. Apparatus $V_2$, in particular at least one of the components selected from the group consisting of water absorption unit $W_{abs2}$, water desorption unit $W_{des2}$, circuit $U_2$, at least partially comprises a surface made of a steel material of construction $O_{st}$ and there is at least one contact surface at which the aqueous liquid absorption medium $A_{VO}$ contacts the surface made of a steel material of construction $O_{st}$. Optionally, circuit $U_2$ may also additionally comprise a pump for conveying the aqueous liquid absorption medium.

Apparatus $V_1$ corresponds to apparatus $V_2$ without absorption medium $A_{VO}$, wherein in the figure description for FIG. 1 and FIG. 2 the terms $U_2$, $W_{abs2}$, $W_{des2}$, $W_{x2}$, $W_{y2}$, $W_{z2}$ are to be replaced by $U_1$, $W_{abs1}$, $W_{des1}$, $W_{x1}$, $W_{y1}$ and $W_{z1}$ respectively.

The process according to the invention will now be illustratively described with reference to apparatus $V_1$ using FIG. 1:

A stream of moist gas mixture G (said stream may for example be moist air, moist natural gas or moist gas mixture originating from the evaporator of an absorption chiller—see also FIG. 2 with regard to this option) is supplied via conduit <101> to a water absorption unit $W_{abs1}$ <103> and contacted there with the aqueous liquid absorption medium $A_{VE}$ supplied to the water absorption unit $W_{abs1}$ <103> via the conduit <105> or via the conduit <113>. The water absorption unit $W_{abs1}$ <103> may be any of the water absorbers recited hereinabove for $W_{abs1}$, in particular a falling-film. Contacting, in the water absorption unit $W_{abs1}$ <103>, gas mixture G supplied via conduit <101> with the aqueous liquid absorption medium $A_{VE}$ supplied via the conduit <105> or via the conduit <113> affords an aqueous liquid absorption medium $A_{VE1}$ having an elevated water content compared to the aqueous liquid absorption medium $A_{VE}$ and a stream of a gas mixture $G_1$ discharged via the conduit <102>, $G_1$ having a relatively low water content compared to the moist gas mixture G. Depending on the application $G_1$ is in particular dehumidified air or dehumidified natural gas. The water absorption unit $W_{abs1}$ <103> may optionally also comprise an additional heat exchanger $W_{z1}$ <104>. Preferably via the conduits <106>, <111> and the heat exchanger $W_{y1}$ <107> (or, when heat exchanger $W_{y1}$ <107> is not employed, via conduits <106>, <111> and <114>) the aqueous liquid absorption medium $A_{VE1}$ is then passed to the water desorption unit $W_{des1}$ composed of the heat exchanger $W_{x1}$ <108> and the water desorber <109>. The water-laden liquid absorption medium $A_{VE1}$ may additionally be supplied with heat in the optional heat exchanger $W_{y1}$ <107>. The at least partial removal of water from aqueous liquid absorption medium $A_{VE1}$ is then carried out in the water desorber <109> to afford an aqueous liquid absorption medium $A_{VE2}$ having a relatively low water content compared to the aqueous liquid absorption medium $A_{VE1}$. The water removed is then discharged from the water desorber <109> as liquid or vapour, preferably as vapour, via a conduit <110>. The aqueous liquid absorption medium $A_{VE2}$ is then discharged from the water desorber <109> and returned to the water absorption unit $W_{abs1}$ <103>. This may either be carried out directly, i.e. via the conduit <113> which is shown in dashed form in FIG. 1. Alternatively and preferably the aqueous liquid absorption medium $A_{VE2}$ may also be supplied via the conduit <112> to the optional heat exchanger $W_{y1}$ <107> in which the aqueous liquid absorption medium $A_{VE1}$ supplied via conduit <106> to the optional heat exchanger $W_{y1}$ <107> is then supplied with heat from the aqueous liquid absorption medium $A_{VE2}$ supplied via conduit <112> to the optional heat exchanger $W_{y1}$ <107>. Once the concentrated aqueous liquid absorption medium $A_{VE2}$ has been supplied to the water absorption unit $W_{abs1}$ via conduit <105> or <113> said medium is reused as $A_{VE}$ for at least partially dehumidifying the gas stream in a new cycle. It is essential to the invention that in this process the apparatus according to FIG. 1, preferably at least one of the components selected from the group consisting of water absorption unit $W_{abs1}$ <103> (in FIG. 1 said unit comprises the heat exchanger <104>), water desorption unit $W_{des1}$ (in FIG. 1 said unit comprises the heat exchanger <108>), circuit $U_1$ (composed in FIG. 1 of the conduits <106>, <111>, <113>, or <106>, <111>, <112>, <105>, and in each case optionally also conduit <114>) at least partially comprises a surface made of a steel material of construction $O_{st}$ and that disposed in the apparatus is at least one contact surface at which at least one of the aqueous liquid absorption media $A_{VE1}$, $A_{VE}$, $A_{VE2}$ contacts the surface made of a steel material of construction $O_{st}$.

FIG. 2 (abbreviated as "FIG. 2") shows in schematic fashion an absorption chiller into which an apparatus $V_2$ is integrated. The constituents <101> to <114> are shown as for the apparatus $V_2$ described in FIG. 1. Additionally, the absorption chiller in FIG. 2 also comprises a condenser <211> which is connected to the water desorption unit $W_{des2}$ <109> via the conduit <110> and is set up for condensing water at least partially removed from the aqueous liquid absorption medium $A_{VO}$ in the water desorption unit $W_{des2}$. Condenser <211> preferably also comprises a heat exchanger <212> with which cooling water may be supplied.

The absorption chiller shown in FIG. 2 also comprises an evaporator <214> connected to the condenser <211> via a conduit <216> (which may optionally comprise a throttling means <213>) and connected via the conduit <101> with the water absorption unit $W_{abs2}$. The evaporator <214> is set up to evaporate condensed water from the condenser. Additionally, the evaporator <214> can further preferably also comprise a heat exchanger <215> which supplies a medium, heat being drawn off from the medium to thus evaporate the condensed water (for example a coolant conduit with, in particular, water as coolant, this coolant being passed into the evaporator <214>).

In an embodiment of the process according to the invention (described hereinbelow with reference to apparatus $V_1$ using FIG. 2) moist gas mixture G originating from evaporator <214> is passed via the conduit <101> to the water absorption unit $W_{abs1}$ <103>. The water removed in water desorption unit $W_{des1}$ is supplied via the conduit <110> to the condenser <211> in which said water is recondensed. A cooling water circuit as heat exchanger <212> installed in the condenser is optionally likewise used therefor. The condensed water is then supplied via a conduit <216> to the evaporator <214> in which the evaporation of water is effected in particular at low pressures, thus bringing about a cooling effect. This may optionally also be effected using a throttling means <213>. This achieves a cooling action in the evaporator <214> and, for example, coolant may be cooled via the heat exchanger <215>. The water vapour generated is then returned to the water absorption unit $W_{abs1}$ <103> via conduit <101>.

The examples which follow are intended to elucidate the present invention without limiting said invention in any way.

EXAMPLES

Inventive examples I1 to I3 and comparative example C1 were carried out.
1. Chemicals Used
EMIM DEP (=ethylmethylimidazolium diethyl phosphate) was obtained from Iolitec.

TEP (=triethyl phosphate) was obtained from Sigma Aldrich.

2. Experimental Procedure 3 drops of the respective solution were dropped onto a steel plate (steel, purity >99.0%) having dimensions of 3 cm×7 cm and a maximum thickness of 3 mm. The contact angle determination was carried out according to SOP 1827. The results are shown in the table which follows.

C1 is the comparative test with a mixture of EMIM DEP and 10 wt % of water, while in the examples I1, I2 and I3 mixtures of EMIM DEP, 10 wt % of water and 10 wt %, 1 wt % and 0.1 wt % of TEP respectively (the wt % values are always based on the total weight of the mixture) were analyzed.

3. Results

| Experiment | solution employed | Contact angle (°) |
|---|---|---|
| C1 | 90 wt % of EMIM DEP + 10 wt % of water | 52.9 |
| I1 | 80 wt % of EMIM DEP + 10 wt % of water + 10 wt % of TEP | 36 |
| I2 | 89 wt % of EMIM DEP + 10 wt % of water + 1 wt % of TEP | 37.2 |
| I3 | 89.9 wt % of EMIM DEP + 10 wt % of water + 0.1 wt % of TEP | 47.5 |

The results show that the inventive absorption media (I1-I3), which comprise a trialkyl phosphate (in this case triethyl phosphate), exhibit a small contact angle to the steel-containing surface compared to those of the prior art (C1). This results in improved surface wetting and thus in greater and more efficient heat exchange in the process according to the invention and the apparatus according to the invention.

All references cited herein are fully incorporated by reference. Having now fully described the invention, it will be understood by those of skill in the art that the invention may be practiced within a wide and equivalent range of conditions, parameters and the like, without affecting the spirit or scope of the invention.

What is claimed is:

1. A process for dehumidifying a moist gas mixture G, in an apparatus ($V_1$), comprising:
   (a) contacting the moist gas mixture G with an aqueous liquid absorption medium $A_{VE}$ comprising a mixture of at least one trialkyl phosphate of structure (I):

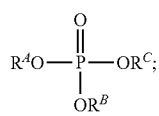

(I)

and at least one salt S selected from the group consisting of $Q^+A^-$, $Q^+(R^1O)_2PO_2^-$, $(Q^+)_2R^2OPO_3^{2-}$, and $Q^+M^+R^3OPO_3^{2-}$,
   wherein $A_{VE}$ at least partially absorbs water from the moist gas mixture G,
   to afford an aqueous liquid absorption medium $A_{VE1}$ having an elevated water content compared to $A_{VE}$ and a gas mixture $G_1$ having a relatively low water content compared to the moist gas mixture G;
   (b) partially removing water from $A_{VE1}$ to obtain an aqueous liquid absorption medium $A_{VE2}$ having a relatively low water content compared to the aqueous liquid absorption medium $A_{VE1}$;
   wherein the apparatus ($V_1$) at least partially comprises a surface made of a steel material of construction $O_{st}$ and, in the apparatus ($V_1$), at least one of the aqueous liquid absorption medium $A_{VE}$, the aqueous liquid absorption medium $A_{VE1}$ and the aqueous liquid absorption medium $A_{VE2}$ contacts the surface made of a steel material of construction $O_{st}$ via at least one contact surface;
   wherein:
   $Q^+$ is a dialkylimidazolium cation,
   $A^-$ is an anion selected from the group consisting of $R^*COO^-$, $R'SO_{3-}$, $HSO_4^-$, $R''SO_4^-$,
   $R^*$, $R'$, $R''$, $R^A$, $R^B$, $R^C$, $R^1$, $R^2$, $R^3$ are each independently of one another an alkyl group, and wherein $M^+$ is an alkali metal ion.

2. The process of claim 1, wherein the gas mixture G is moist air.

3. The process of claim 1, wherein:
   a) $Q^+$ is a dialkylimidazolium cation in which the alkyl groups each independently of one another have 1 to 10 carbon atoms;
   b) $R^*$, $R'$, $R''$, $R^A$, $R^B$, $R^C$, $R^1$, $R^2$, $R^3$ are each independently of one another an alkyl group having 1 to 10 carbon atoms; and
   c) $M^+$=$Li^+$, $K^+$ or $Na^+$.

4. The process of claim 1, wherein:
   a) salt S is selected from the group consisting of: $Q^+A^-$ and $Q^+(R^1O)_2PO_2^-$;
   b) $Q^+$ is a dialkylimidazolium cation in which the alkyl groups each independently of one another have 1 to 6 carbon atoms; and
   c) $A^-$ is an anion selected from the group consisting of $R^*COO^-$, $R'SO_3^-$, and $R''SO_4^-$, and
   d) $R^*$, $R^1$, $R'$, $R''$, $R^A$, $R^B$, $R^C$ are each independently of one another an alkyl group having 1 to 6 carbon atoms.

5. The process of claim 1, wherein $R^A$, $R^B$, $R^C$ are independently of one another selected from the group consisting of: methyl and ethyl.

6. The process of claim 1, wherein the aqueous liquid absorption medium $A_{VE}$ is an aqueous solution, and the total weight of all trialkyl phosphates of structure (I) and all salts S is in the range 65 wt % to 95 wt % based on the total weight of the aqueous solution.

7. The process of claim 1, wherein, in the aqueous liquid absorption medium $A_{VE}$, the ratio of the total weight of all trialkyl phosphates of structure (I) to the total weight of all salts S is in the range 1:9999 to 1:9.

8. The process of claim 3, wherein $R^A$, $R^B$, and $R^C$ are independently of one another selected from the group consisting of: methyl and ethyl.

9. The process of claim 8, wherein the aqueous liquid absorption medium $A_{VE}$ is an aqueous solution, and the total weight of all trialkyl phosphates of structure (I) and all salts S is in the range 65 wt % to 95 wt % based on the total weight of the aqueous solution.

10. The process of claim 9, wherein, in the aqueous liquid absorption medium $A_{VE}$, the ratio of the total weight of all trialkyl phosphates of structure (I) to the total weight of all salts S is in the range 1:9999 to 1:9.

11. An apparatus, ($V_2$), for dehumidifying a moist gas mixture, comprising the components:

(i) an aqueous liquid absorption medium, $A_{VO}$, which comprises a mixture of at least one trialkyl phosphate of structure (I):

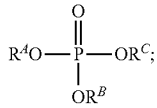

$$R^AO-\underset{\underset{OR^B}{|}}{\overset{\overset{O}{\|}}{P}}-OR^C;\quad (I)$$

and at least one salt, S, selected from the group consisting of: $Q^+A^-$, $Q^+(R^1O)_2PO_2^-$, $(Q^+)_2R^2OPO_3^{2-}$, and $Q^+M^+R^3OPO_3^{2-}$;
(ii) at least one water absorption unit, $(W_{abs2})$, set up for contacting the moist gas mixture with the aqueous liquid absorption medium $A_{VO}$;
(iii) at least one water desorption unit, $(W_{des2})$, which comprises a heat exchanger, $(W_{x2})$, and is set up for at least partially removing water from an aqueous liquid absorption medium $A_{VO}$; and
(iv) a circuit, $(U_2)$, which connects the water absorption unit $(W_{abs2})$ with the water desorption unit $(W_{des2})$ and by means of which the aqueous liquid absorption medium $A_{VO}$ may be circulated,
wherein at least one of the components selected from the group consisting of: the water absorption unit $(W_{abs2})$; the water desorption unit $(W_{des2})$; and the circuit $(U_2)$, at least partially comprises a surface made of a steel material of construction $O_{ST}$;
wherein, disposed in the apparatus $(V_2)$, is at least one contact surface at which the aqueous liquid absorption medium $A_{VO}$ contacts the surface made of a steel material of construction $O_{st}$;
and wherein:
$Q^+$ is a dialkylimidazolium cation;
$A^-$ is an anion selected from the group consisting of $R^*COO^-$, $R'SO_{3-}$, $HSO_4^-$, $R''SO_4^-$;
$R^*$, $R'$, $R''$, $R^A$, $R^B$, $R^C$, $R^1$, $R^2$, $R^3$ are each independently of one another an alkyl group; and
$M^+$ is an alkali metal ion.
12. The apparatus $(V_2)$ of claim 11, wherein:
a) $Q^+$ is a dialkylimidazolium cation in which the alkyl groups each independently of one another have 1 to 10 carbon atoms;
b) $R^*$, $R'$, $R''$, $R^A$, $R^B$, $R^C$, $R^1$, $R^2$, $R^3$ are each independently of one another an alkyl group having 1 to 10 carbon atoms; and
c) $M^+=Li^+$, $K^+$ or $Na^+$.
13. The apparatus $(V_2)$ of claim 11, wherein:
a) salt S is selected from the group consisting of: $Q^+A^-$, and $Q^+(R^1O)_2PO_2^-$;
b) $Q^+$ is a dialkylimidazolium cation in which the alkyl groups each independently of one another have 1 to 6 carbon atoms;
c) $A^-$ is an anion selected from the group consisting of $R^*COO^-$, $RSO_3^-$, and $R''SO_4^-$, and
d) $R^*$, $R^1$, $R'$, $R''$, $R^A$, $R^B$, $R^C$ are each independently of one another an alkyl group having 1 to 6 carbon atoms.
14. The apparatus $(V_2)$ of claim 11, wherein $R^A$, $R^B$ and $R^C$ are independently of one another selected from the group consisting of: methyl and ethyl.
15. The apparatus $(V_2)$ of claim 11, wherein the aqueous liquid absorption medium $A_{VO}$ is an aqueous solution, and, the total weight of all trialkyl phosphates of structure (I) and all salts S is in the range 65 wt % to 95 wt % based on the total weight of the aqueous solution.
16. The apparatus $(V_2)$ of 11, wherein, in the aqueous liquid absorption medium $A_{VO}$, the ratio of the total weight of all trialkyl phosphates of structure (I) to the total weight of all salts S is in the range 1:9999 to 1:9.
17. The apparatus of claim 12, wherein $R^A$, $R^B$, $R^C$ are independently of one another selected from the group consisting of: methyl and ethyl.
18. The apparatus of claim 17, wherein the aqueous liquid absorption medium $A_{VO}$ is an aqueous solution, and, the total weight of all trialkyl phosphates of structure (I) and all salts S is in the range 65 wt % to 95 wt % based on the total weight of the aqueous solution.
19. The apparatus of claim 18, wherein, in the aqueous liquid absorption medium $A_{VO}$ the ratio of the total weight of all trialkyl phosphates of structure (I) to the total weight of all salts S is in the range 1:9999 to 1:9.
20. An absorption heat pump, comprising the apparatus $(V_2)$ of claim 11 and further comprising a condenser, an evaporator and a coolant, wherein the coolant is water.

* * * * *